(12) United States Patent
Dai et al.

(10) Patent No.: US 10,973,685 B2
(45) Date of Patent: Apr. 13, 2021

(54) SYSTEMS AND METHODS FOR REDUCING SPHERICAL ABERRATION USING PERIPHERY MODIFICATION

(71) Applicant: AMO Development, LLC, Santa Ana, CA (US)

(72) Inventors: Guang-ming Dai, Fremont, CA (US); Dimitri Chernyak, Belmont, MA (US); Sanjeev Kasthurirangan, Fremont, CA (US)

(73) Assignee: AMO Development, LLC, Santa Ana, CA (US)

( * ) Notice: Subject to any disclaimer, the term of this patent is extended or adjusted under 35 U.S.C. 154(b) by 166 days.

(21) Appl. No.: 16/206,409

(22) Filed: Nov. 30, 2018

(65) Prior Publication Data

US 2019/0167477 A1    Jun. 6, 2019

Related U.S. Application Data

(60) Provisional application No. 62/593,621, filed on Dec. 1, 2017.

(51) Int. Cl.
*A61F 9/008* (2006.01)
*A61F 9/009* (2006.01)
(Continued)

(52) U.S. Cl.
CPC .......... *A61F 9/00804* (2013.01); *A61B 3/103* (2013.01); *A61B 3/14* (2013.01);
(Continued)

(58) Field of Classification Search
CPC .. A61F 9/00804; A61F 9/00817; A61F 9/009; A61F 2009/00863; A61F 9/00812;
(Continued)

(56) References Cited

U.S. PATENT DOCUMENTS

| | | | |
|---|---|---|---|
| 4,665,913 A | 5/1987 | L'Esperance, Jr. |
| 4,669,466 A | 6/1987 | L'Esperance |

(Continued)

OTHER PUBLICATIONS

Dai G., Wavefront Optics for Vision Correction, SPIE Press, Chapter. 2, 2008.
(Continued)

*Primary Examiner* — Rex R Holmes
(74) *Attorney, Agent, or Firm* — Johnson & Johnson Surgical Vision, Inc.

(57) ABSTRACT

A system for determining a vision treatment for an eye of a patient is provided which includes a memory and a processor, in communication with the memory, configured to receive a first treatment target corresponding to a first target shape of a surface of the eye, obtain a periphery modification function (PMF), determine a second treatment target corresponding to a second target shape of the surface of the eye by multiplying, for each of a plurality of points on the surface of the eye, the PMF by the first treatment target, and scale the second treatment target using a scaling factor such that values of the second treatment target are scaled to be greater at a mid-periphery of the eye and scaled to be lower at a far-periphery of the eye. A treatment parameter of a treatment applied to the surface of the eye is controlled by the scaled second treatment target.

20 Claims, 11 Drawing Sheets

(51) Int. Cl.
*B23K 26/08* (2014.01)
*A61B 3/14* (2006.01)
*A61B 3/103* (2006.01)

(52) U.S. Cl.
CPC .......... *A61F 9/009* (2013.01); *A61F 9/00817* (2013.01); *B23K 26/08* (2013.01); *A61F 9/00812* (2013.01); *A61F 2009/00863* (2013.01); *A61F 2009/00872* (2013.01); *A61F 2009/00897* (2013.01)

(58) Field of Classification Search
CPC . A61F 2009/00872; A61F 2009/00897; B23K 26/08; A61B 3/14; A61B 3/103
See application file for complete search history.

(56) References Cited

U.S. PATENT DOCUMENTS

| | | | |
|---|---|---|---|
| 4,732,148 A | 3/1988 | L'Esperance, Jr. | |
| 4,770,172 A | 9/1988 | L'Esperance, Jr. | |
| 4,773,414 A | 9/1988 | L'Esperance, Jr. | |
| 5,108,388 A | 4/1992 | Trokel | |
| 5,207,668 A | 5/1993 | L'Esperance, Jr. | |
| 5,219,343 A | 6/1993 | L'Esperance, Jr. | |
| 5,258,791 A | 11/1993 | Penney et al. | |
| 5,646,791 A | 7/1997 | Glockler | |
| 5,683,379 A | 11/1997 | Hohla | |
| 5,713,892 A | 2/1998 | Shimmick | |
| 5,807,379 A | 9/1998 | L'Esperance, Jr. | |
| 6,000,800 A | 12/1999 | Webb et al. | |
| 6,004,313 A | 12/1999 | Shimmick et al. | |
| 6,095,651 A | 8/2000 | Williams et al. | |
| 6,099,125 A | 8/2000 | Webb et al. | |
| 6,203,539 B1 | 3/2001 | Shimmick et al. | |
| 6,271,915 B1 | 8/2001 | Frey et al. | |
| 6,315,413 B1 | 11/2001 | Shimmick et al. | |
| 6,331,177 B1 | 12/2001 | Munnerlyn et al. | |

OTHER PUBLICATIONS

Fabrikant A., et al., "Optimization of Linear Filtering Model to Predict Post-Lasik Corneal Smoothing Based on Training Date Sets," Applied Mathematics, Dec. 2013, vol. 4, pp. 1694-1701.

SYSTEMS AND METHODS FOR REDUCING SPHERICAL ABERRATION USING PERIPHERY MODIFICATION

CROSS REFERENCE TO RELATED APPLICATION

This application claims the benefit of U.S. Provisional Application No. 62/593,621, filed on Dec. 1, 2017, which is incorporated by reference as if fully set forth.

SUMMARY

Embodiments described herein are related to the field of vision treatment, and in particular, to systems and methods for generating or modifying optical treatment shapes.

A computer implemented method of determining a vision treatment for an eye of a patient is provided which includes receiving a first treatment target for the eye of the patient and obtaining a periphery modification function (PMF). The method also includes multiplying, for each of a plurality of points on a surface of the eye, the PMF by the first treatment target, to produce a modified treatment target. The method further includes scaling the second treatment target using a scaling factor such that values of the second treatment target are scaled to be greater at a mid-periphery of the eye and scaled to be lower at a far-periphery of the eye. A treatment parameter of a treatment applied to the surface of the eye is controlled by the scaled second treatment target.

A system for determining a vision treatment for an eye of a patient is provided which includes a memory configured to store programmed instructions and data and a processor in communication with the memory. The processor is configured to receive a first treatment target for the eye of the patient. The processor is also configured to obtain a PMF and multiply, for each of a plurality of points on a surface of the eye, the PMF by the first treatment target, to produce a modified treatment target. The processor is also configured to scale the second treatment target using a scaling factor such that values of the second treatment target are scaled to be greater at a mid-periphery of the eye and scaled to be lower at a far-periphery of the eye. A treatment parameter of a treatment applied to the surface of the eye is controlled by the scaled second treatment target.

A non-transitory computer readable medium is provided which includes instructions for causing a computer to execute a method of determining a vision treatment for an eye of a patient. The instructions include receiving a first treatment target corresponding to a first target shape of a surface of the eye, obtaining a periphery modification function (PMF), determining a second treatment target corresponding to a second target shape of the surface of the eye by multiplying, for each of a plurality of points on the surface of the eye, the PMF by the first treatment target and scaling the second treatment target using a scaling factor such that values of the second treatment target are scaled to be greater at a mid-periphery of the eye and scaled less at a far-periphery of the eye. A treatment parameter of a treatment applied to the surface of the eye is controlled by the scaled second treatment target. A treatment parameter of a treatment applied to the surface of the eye is controlled by the scaled second treatment target.

BRIEF DESCRIPTION OF THE DRAWINGS

A more detailed understanding can be had from the following description, given by way of example in conjunction with the accompanying drawings wherein.

DETAILED DESCRIPTION OF THE PREFERRED EMBODIMENTS

Figure 1:
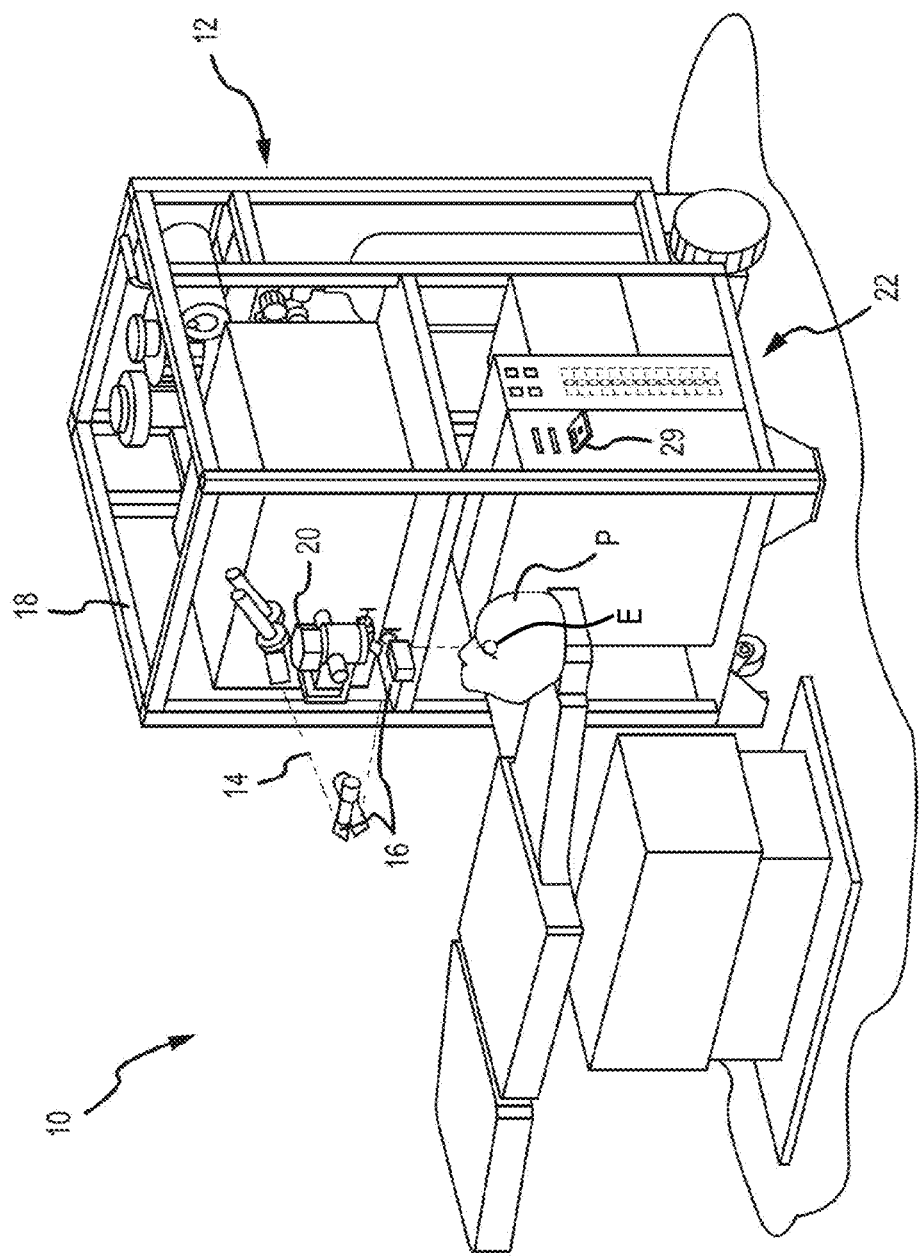
FIG. 1 illustrates a laser ablation system according to an embodiment described herein.

Refractive eye surgery has been determined, in some cases, to induce some aberrations. For example, it is believed that laser-assisted in situ keratomileusis (LASIK) surgeries can induce high order aberrations, such as spherical aberration which can affect night vision. SA involves off-axis rays entering the eye with different heights of focus at different locations. Although a specific cause for the induction of the SA has not yet been identified, a combination of different factors, such as biomechanical effect, healing and inappropriate treatment algorithms (e.g., algorithms which do not account for the "cosine effect" as described in Guang-ming Dai, Wavefront Optics for Vision Correction (SPIE Press, 2008), Chap. 2.) have been determined to contribute to the cause of the inductions.

Conventional techniques for reducing SA induction include a mathematical filtering and deconvolution to compensate for SA induction, as described in Anatoly Fabrikant, Guang-ming Dai, and Dimitri Chernyak, "Optimization of linear filtering model to predict post-LASIK corneal smoothing based on training data," Applied Mathematics 4, 1694-1701 (2013).

Embodiments disclosed herein provide systems and methods which utilize a scalable approach for reducing SA. A single parameter PMF is used to construct a two-dimensional function which is multiplied by a treatment target point-by-point to provide a modified treatment target. The modified treatment target is scaled according to a scaling factor. The single parameter (e.g., strength) is adjusted to increase mid-periphery ablation and decrease far-periphery ablation. A modified treatment target slope is determined from previously generated data. The value (e.g., adjustment value) of the single parameter is determined, via a simulation model, using the modified treatment target slope.

The techniques disclosed herein can be readily adapted for use with existing laser systems. By providing a more accurate (and hence, for example, less variable) methodology for treating optical errors of an eye, embodiments described herein facilitate sculpting of the cornea or other opthalmological tissues so that treated eyes may consistently and reliably receive the desired optical correction resulting in improved vision.

Embodiments described herein can be readily adapted for use with existing laser systems and other optical treatment devices. Although system, software, and method embodiments are described primarily in the context of a laser eye surgery system, it should be understood that embodiments may be adapted for use in or in combination with alternative eye treatment procedures, systems, or modalities, such as spectacle lenses, intraocular lenses, accommodating IOLs, contact lenses, corneal ring implants, collagenous corneal tissue thermal remodeling, corneal inlays, corneal onlays, other corneal implants or grafts, and the like. Relatedly, systems, software, and methods according to embodiments are well suited for customizing any of these treatment modalities to a specific patient. Thus, for example, embodiments encompass custom preformed lenses, intraocular lenses, custom contact lenses, custom corneal implants, and the like, which can be configured to treat or ameliorate any of a variety of vision conditions in a particular patient based on their unique ocular characteristics or anatomy. Additionally, the modified ablation target or target shape may be implemented via other non-ablative laser therapies, such as laser-incised custom lenticule shapes and subsequent extraction and laser-based corneal incision patterns.

Some embodiments disclosed herein can be carried out in conjunction with treatments provided by any of a variety of laser devices, including without limitation the WaveScan® System and the STAR S4® Excimer Laser System both by Abbott Medical Optics Inc., the WaveLight® Allegretto Wave® Eye-Q laser, the Schwind Amaris™ lasers, the 217P excimer workstation by Technolas PerfectVision GmbH, the Mel 80™ laser by Carl Zeiss Meditec, Inc., and the like.

Turning now to the drawings, FIG. 1 illustrates a laser eye surgery system 10, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. Embodiments described herein may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used.

The exemplary laser system 10 includes a computer processing device 22. Processing device 22 may include one or more processors, user interface devices such as a keyboard, a display monitor, and the like. Processing device 22 may also include memory (e.g., volatile or non-volatile memory) and a storage device, such as a floppy disk, an optical disk, a data tape, a magnetic or optical disk drive. Processing device 22 may also include a network interface (e.g., network interface controller) configured to communicate with a wired or wireless network. Tangible storage media 29 may take the form of a floppy disk, an optical disk, a data tape, a volatile or non-volatile memory, RAM, or the like. One or more processors of the processing device 22 can be used to process (e.g., fetch, read, write, store and execute) programmed instructions (e.g., modules) stored on the tangible storage media 29 to perform any of the methods described herein. Tangible storage media 29 may optionally embody wavefront sensor data, wavefront gradients, a wavefront elevation map, a treatment map, a corneal elevation map, and/or an ablation table. Processing device 22 may be configured to receive programmed instructions from tangible storage media 29 via a physical input device (e.g., port) of processing device 22, as well as remotely from tangible storage media 29 via one or more wired networks (e.g., Ethernet) or wireless networks (e.g., via wireless protocols such as as infrared, Bluetooth, Wi-Fi or the like).

Laser 12 and delivery optics 16 will generally direct laser beam 14 to the eye of patient P under the direction of processing device 22. Processing device 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processing device 22 to effect the desired laser sculpting process, with the processing device effecting (and optionally modifying) the pattern of laser pulses. The pattern of pulses may by summarized in machine readable data of tangible storage media 29 in the form of a treatment table, and the treatment table may be adjusted according to feedback input into processing device 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processing device 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
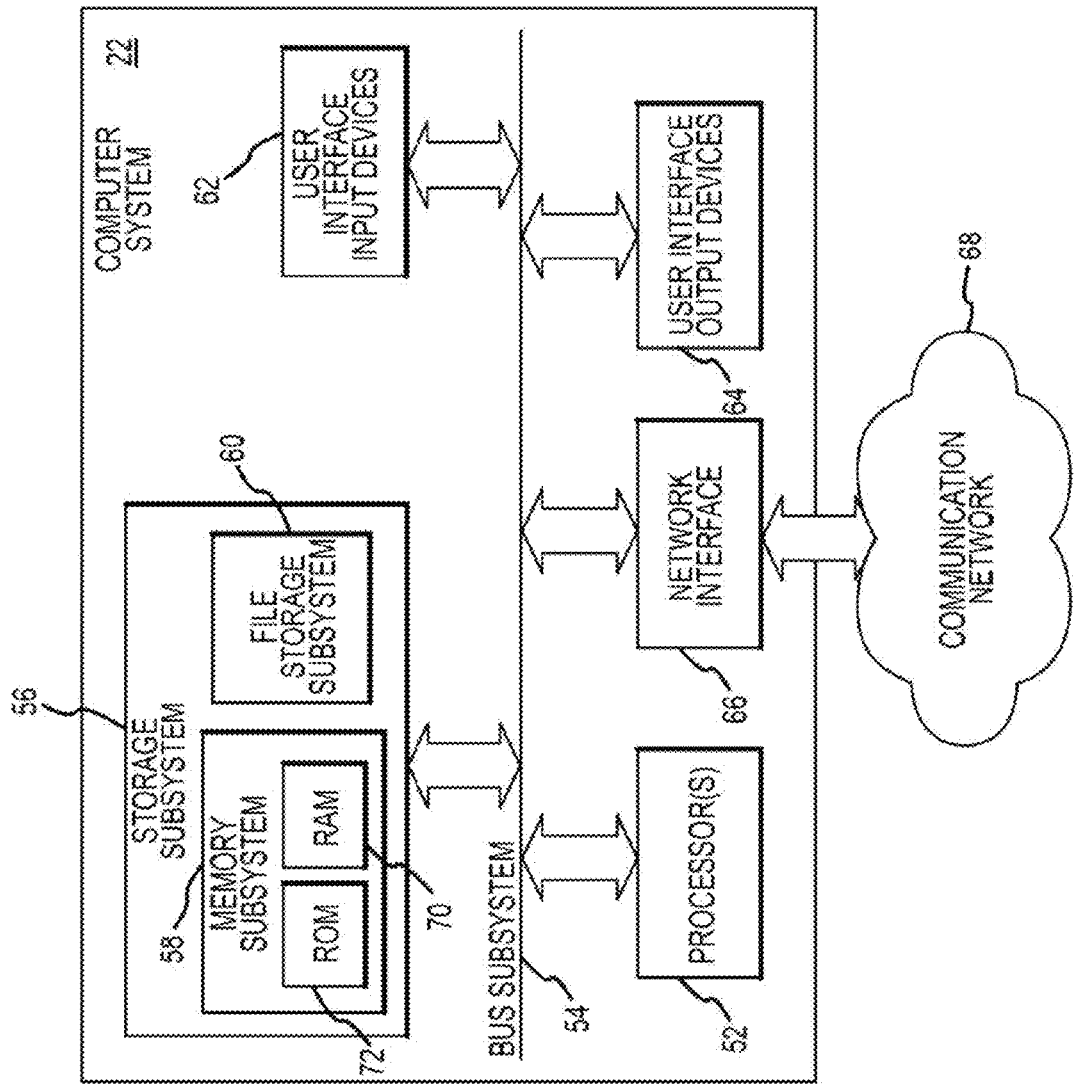
FIG. 2 illustrates a simplified computer system according to an embodiment described herein.

FIG. 2 is a simplified block diagram of an example computer system (i.e., processing device) 22 that may be used by the laser surgical system 10. Processing device 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods. In general, use of the term "input device" is intended to include a variety of conventional and proprietary devices and ways to input information into processing device.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from processing device 22 to a user.

Storage subsystem 56 can store the basic programming and data constructs that provide the functionality of the various embodiments. For example, a database and modules implementing the functionality of the methods, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (e.g., as shown in FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to processing device 22. The modules implementing the functionality may be stored by file storage subsystem 60.

Bus subsystem 54 provides a mechanism for letting the various components and subsystems of processing device 22 communicate with each other as intended. The various subsystems and components of processing device 22 need not be at the same physical location but may be distributed at various locations within a distributed network. Although bus subsystem 54 is shown schematically as a single bus, alternate embodiments of the bus subsystem may utilize multiple busses.

Processing device 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of processing device 22 depicted in FIG. 2 is intended only as a specific example for purposes of illustrating one embodiment. Many other configurations of processing device 22 are possible having more or less components than the processing device depicted in FIG. 2.

Figure 3:
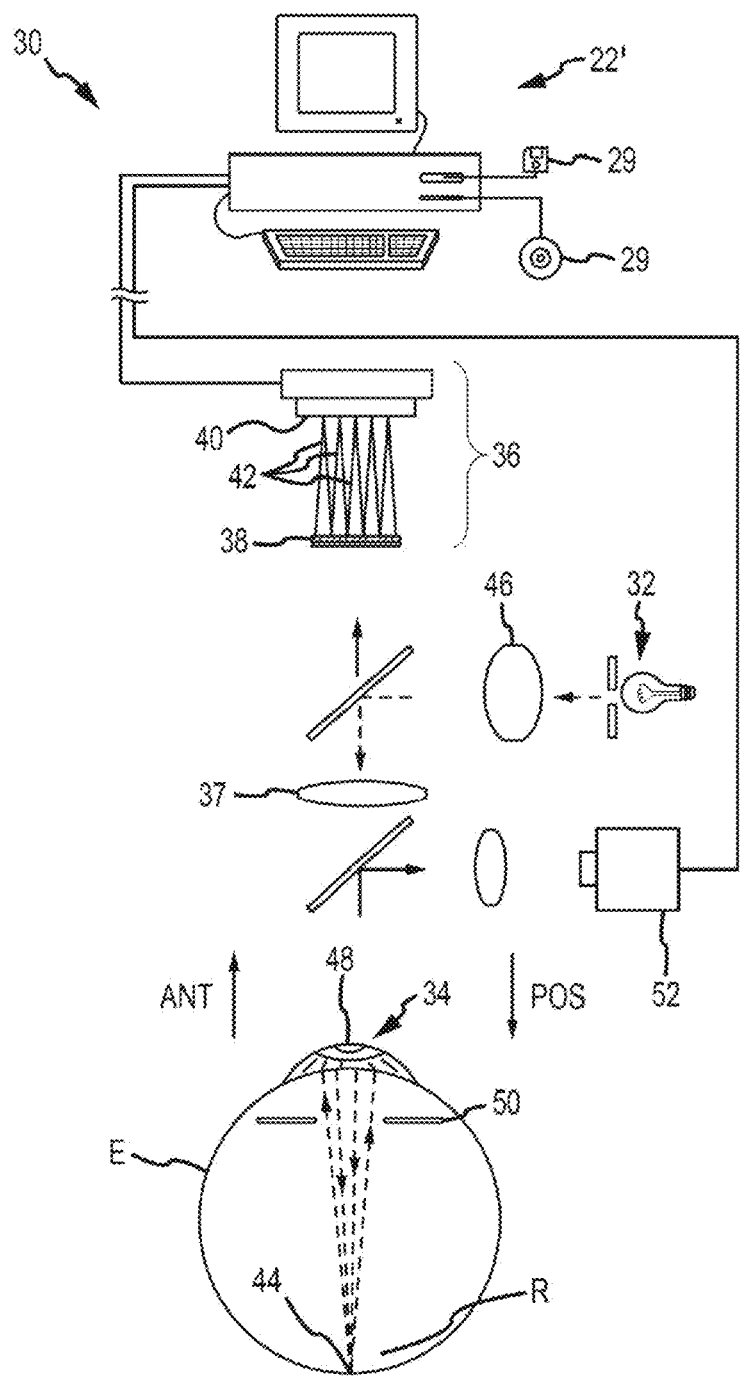
FIG. 3 illustrates a wavefront measurement system according to an embodiment described herein.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer system 22' may include the same or similar hardware as the processing device 22 illustrated in FIGS. 1 and 2. Computer system 22' may be in communication with processing device 22, which directs the laser surgery system 10, or some or all of the components of processing device 22. Processing device 22 and computer system 22' may be combined or separate. If desired, data from wavefront sensor 36 may be transmitted to processing device 22 via tangible media 29, via an I/O port, via a networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil 50 is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 52 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the example embodiment, a pupil camera 52 images pupil 50 so as to determine a position of the pupil 50 for registration of the wavefront sensor data relative to the optical tissues.

Figure 3A:
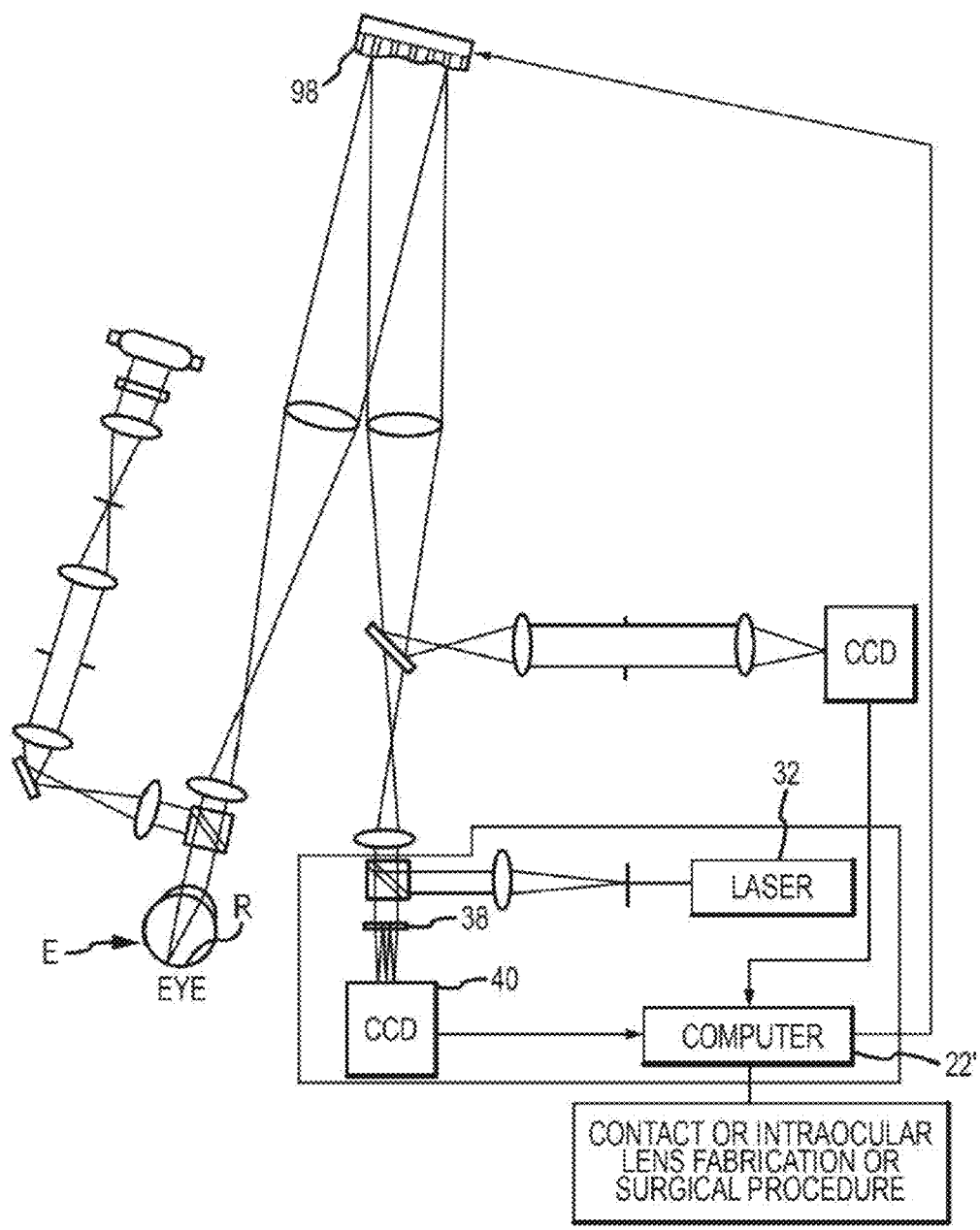
FIG. 3A illustrates another wavefront measurement system according to another embodiment described herein.

An alternative embodiment of a wavefront measurement system is illustrated in FIG. 3A. The major components of the system of FIG. 3A are similar to those of FIG. 3. Additionally, FIG. 3A includes an adaptive optical element in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22' to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a WaveScan® System. One embodiment includes a WaveScan® System with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with embodiments disclosed herein.

Figure 4:
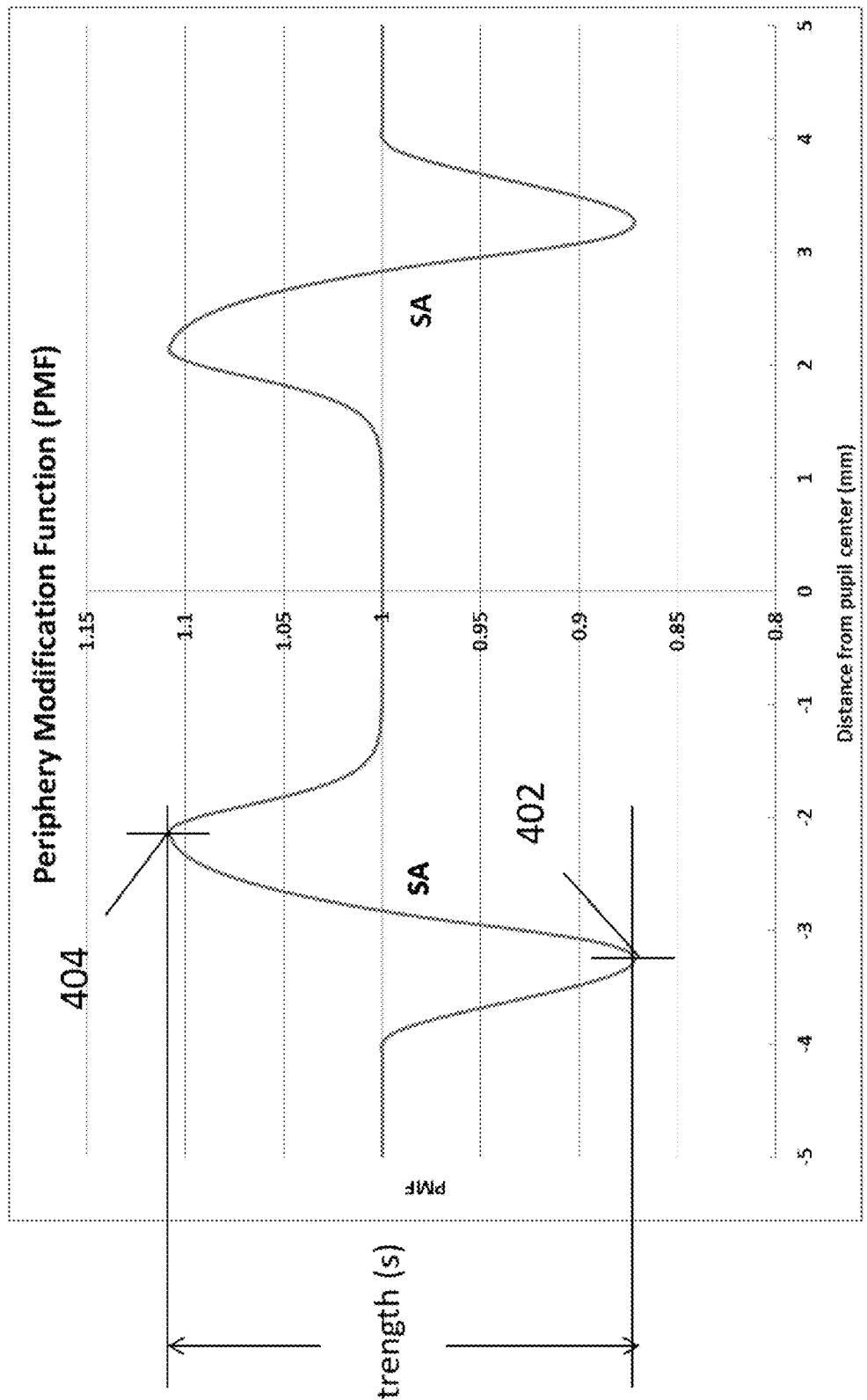
FIG. 4 is a cross sectional graph of an exemplary PMF, illustrating the PMF as a rotationally symmetrical two-dimensional function according to embodiments described herein.

FIG. 4 is an example cross sectional graph of a PMF, illustrating the PMF as a rotationally symmetrical two-dimensional function. The X-axis values correspond to the distance (in mm) at any point on the eye from the center of the eye (i.e., pupil center). The Y-axis values correspond to arbitrary non-unit scaling factor. As shown in FIG. 4, these scaling factor values fluctuate around a value of 1 on the Y-axis.

For simplification purposes, the PMF is now described with reference to the left side of FIG. 4. As shown in FIG. 4, the function is mirrored on the right side to illustrate the rotationally symmetrical attribute. The PMF includes a bottom point 402 corresponding to scaling factor value of about 0.87 and a top point 404 corresponding to scaling factor value of about 1.11. As the points on the surface of the eye move further away (i.e., to the left) from the center of the eye, the PMF first includes a flat central area, followed by a mid-periphery area in which ablation is increased to point 404, followed by a decrease of ablation to point 402.

As a basis for estimating the PMF, the following Equation 1 is used:

$$T \cdot M - T = sa \quad \text{Equation 1}$$

In Equation 1, T is the treatment target, M is the PMF, and sa is the induced SA. The modification function M is estimated as a function which increases ablation in the mid-periphery (corresponding to the regions on the graph in FIG. 4 in which the points on the PMF correspond to scaling factors above 1) and decreases ablation in the far-periphery (corresponding to regions on the graph in FIG. 4 in which the points on the PMF correspond to scaling factors below 1) in order to match the observations. The ablation of the treatment target (i.e., target shape of the optical surface) is increased more at the mid-periphery of the eye and decreased more at the far-periphery of the eye by adjusting a single parameter, the strength of the PMF.

As shown in FIG. 4, as the function moves away from the pupil center (x=0), points along the eye in the central portion correspond to a scaling factor value at or near 1. As the function moves away from the pupil center, points along the eye in the mid-periphery correspond to a scaling factor values greater than 1. In the mid-periphery, the function increases to point 404 (i.e., a top of the PMF) corresponding to scaling factor value of about 1.11 and then decreases until it reaches a point corresponding to scaling factor value of 1. In the far-periphery, the function continues to decrease to point 402 (i.e., a bottom of the PMF) corresponding to scaling factor value of about 0.87 and then increases until it reaches a point corresponding to scaling factor value of 1.

The product of the PMF and a first treatment target results in a second treatment target), which can be used to control a treatment parameter, such as an ablation depth. When any value is multiplied by 1, the product is the same as the value. Accordingly, when the PMF is multiplied by a first treatment target (e.g., an original treatment target) point-by-point, a value of 1 indicates no change to the treatment parameter. Values that are greater than 1 indicate increasing the treatment parameter and values below 1 indicate decreasing the treatment parameter. For example, if the first or previous determination is to ablate at a depth of 100 for a treatment target point on the optical surface corresponding to a scaling factor value of 1.1 on the PMF graph in FIG. 4, the resulting product of the PMF to the treatment target point (i.e., the second treatment target) indicates that the ablation depth should be changed to 110 (i.e., 100×1.1). As described in more detail below, the strength s of the PMF (i.e., difference between bottom 402 and top 404 of the PMF function) may be adjusted based on a determination of the target slope.

Figure 5B:
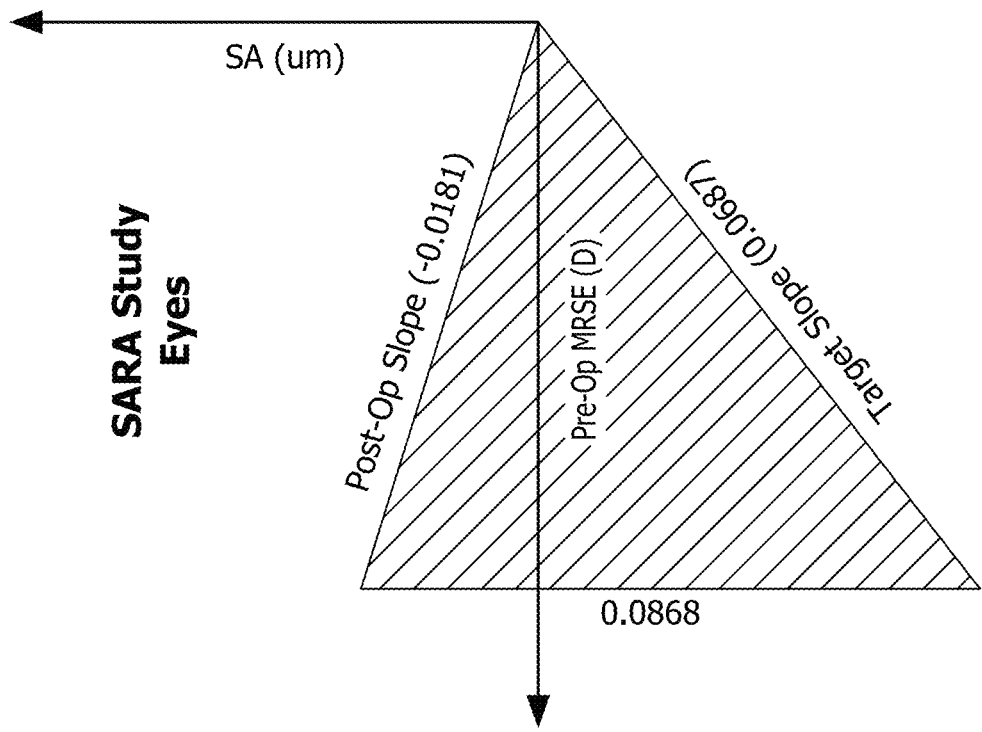
FIG. 5B is a graphical illustration showing a change to the post-operation slope and the target slope of one of the studies shown in FIG. 5A.
Figure 5A:
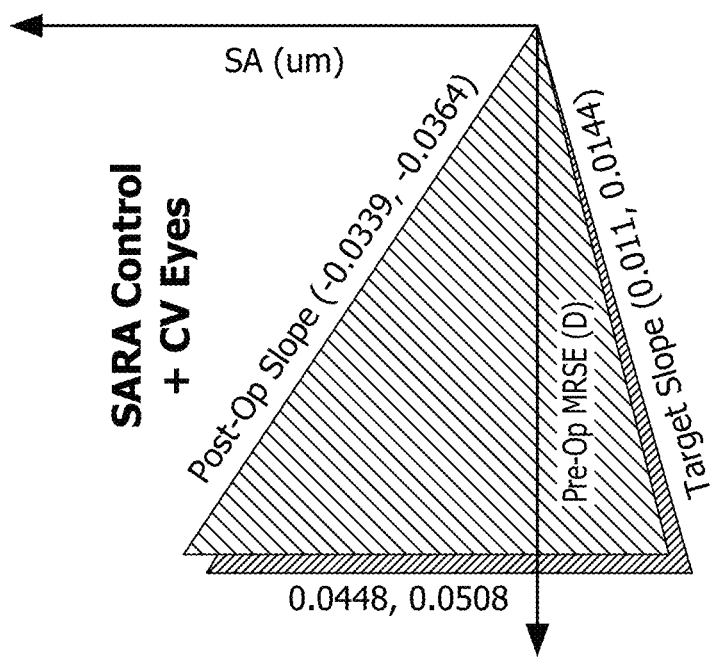
FIG. 5A is a graphical illustration showing a post-operation slope and a target slope for two different studies according to embodiments described herein.

FIGS. 5A and 5B are graphical representations of post-operation slopes and target slopes for different studies. FIG. 5A illustrates post-operation and target slopes for 2 studies (i.e., spherical aberration reduction algorithm (SARA) Control study and iDesign CustuomVue (CV) study). As shown in FIG. 5A, the post-operation slope (i.e., slope of the spherical aberration as a function of the pre-operation MRSE) is about −0.0339 for the SARA Control study and the post-operation slope for the iDesign CV study is about −0.0364.

During the SARA Control study, the slope was changed. FIG. 5B illustrates the changed post-operation slope (−0.0181) and the target slope. Refractive surgery bends the slope from pre-op to post-op. For the SARA Control and the iDesign CV studies, the pre-op slope was about 0.01 (0.011 for SARA Control and 0.0144 for iDesign CV). Accordingly, the slope change (i.e., bending) is about 0.05 (0.011−(−0.0339)=0.448 for SARA Control; 0.01444−0.0364)=0.0508 for iDesign CV). For the SARA study, the bending is about 0.0868 (0.06874−0.0181)=0.0868). Using the graphical illustration in FIG. 5A and FIG. 5B, the amount of slope change (i.e., slope bending) can be determined to cause the post-op slope to be zero. That is, as shown in FIG. 5A, the post-operation slope values for the 2 studies are close to each other.

Figure 6:
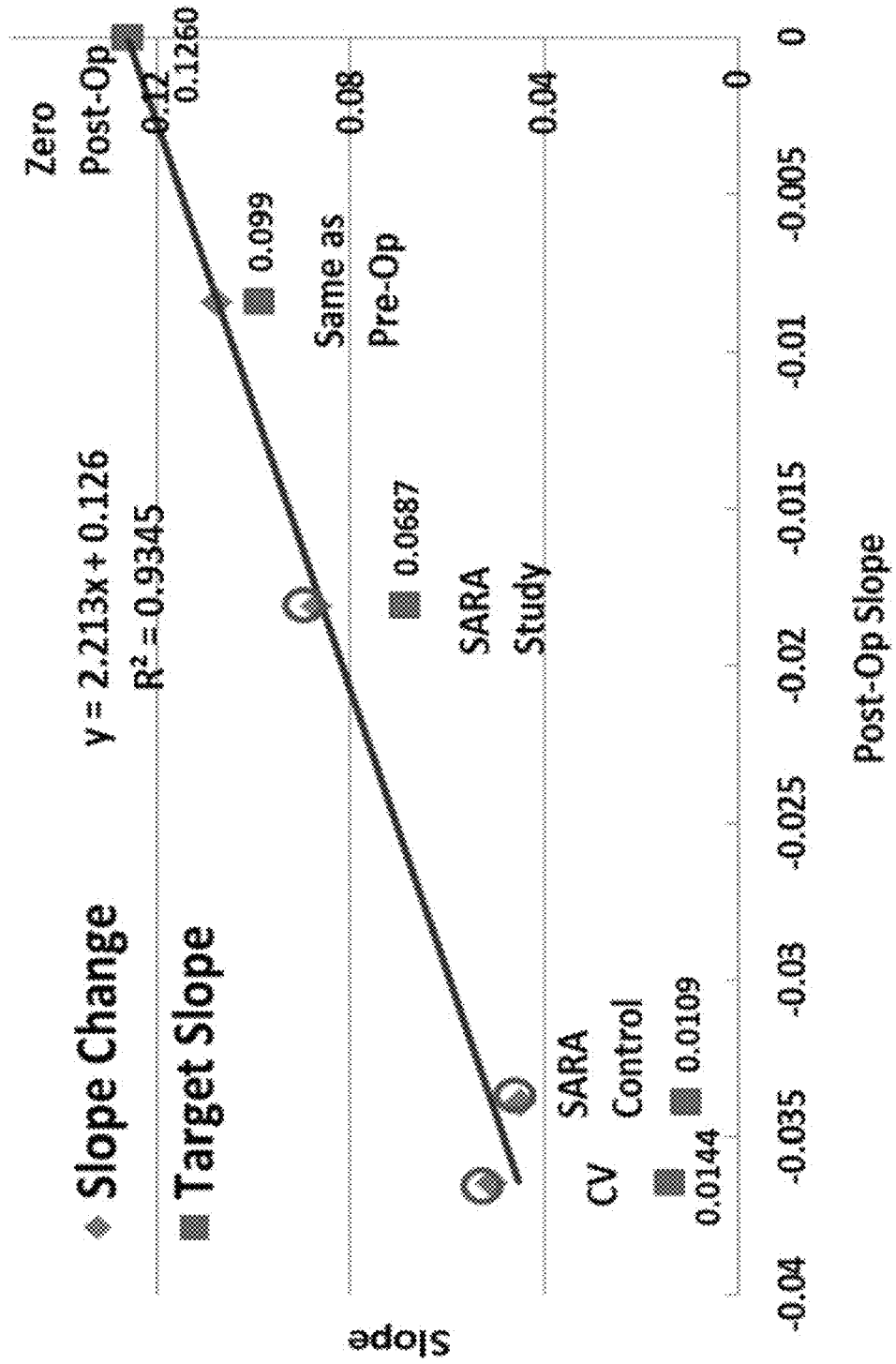
FIG. 6 is a graphical illustration of three observations for the target slopes and the corresponding change of the slopes according to embodiments described herein.

FIG. 6 is a graphical illustration of observations for the target slopes and the corresponding change of the slopes for the iDesign CV study, the SARA control eyes, and the SARA study eyes. Because it is assumed that the slope in the target is linearly related to the change of the slope, the pre-op slope can be determined. Two separate outcomes are considered: (1) the post-op SA is the same as pre-op SA; and (2) the post-op SA is zero. Based on the determination of the pre-op slope, the target slope for outcome (1) is about 0.099 and the target slope for outcome (20 is 0.126, respectively, as shown in FIG. 6.

Figure 7:
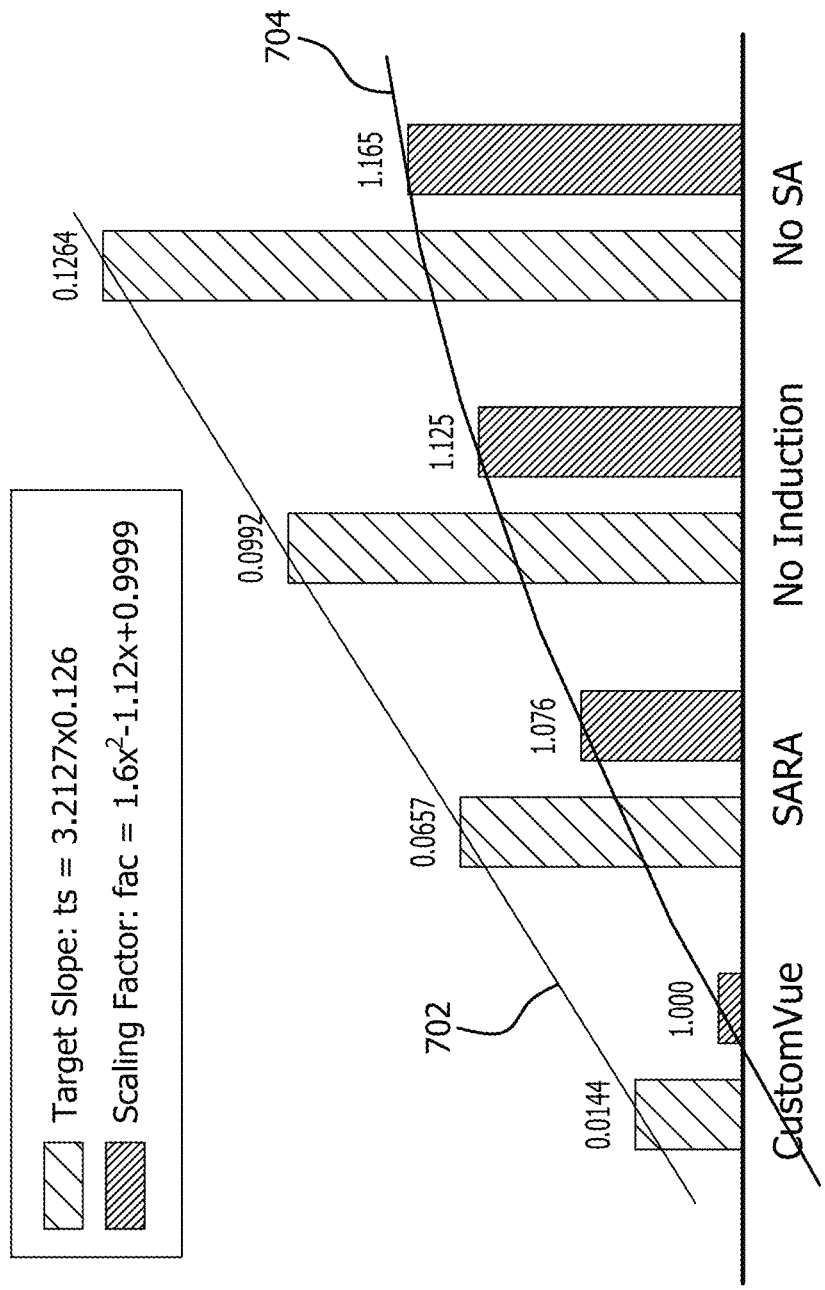
FIG. 7 is a graph illustrating a target slope and the scaling of the target slope.

FIG. 7 is a graph illustrating the target slope and the scaling of the target slope for the CV study, the SARA study, no induction and no SA. The graph shown in FIG. 7 indicates that the target slope is a linear function of the desired or observed post operation slope. The plot of the linear function is indicated by line 704 in FIG. 7. It is desirable to maintain the refraction over a pupil (e.g., 4 mm pupil) between different algorithms (e.g., algorithm used in the CV study vs. SA-reduction algorithm) to facilitate non-altering the goal of emmetropia. Accordingly, after the multiplication of the PMF, the target is scaled uniformly and the refraction is maintained. The scaling factor is determined, through simulation, to be a quadratic function of the post-op desired or observed slope, the plot of the quadratic function being indicated by line 704 in FIG. 7.

Figure 8:
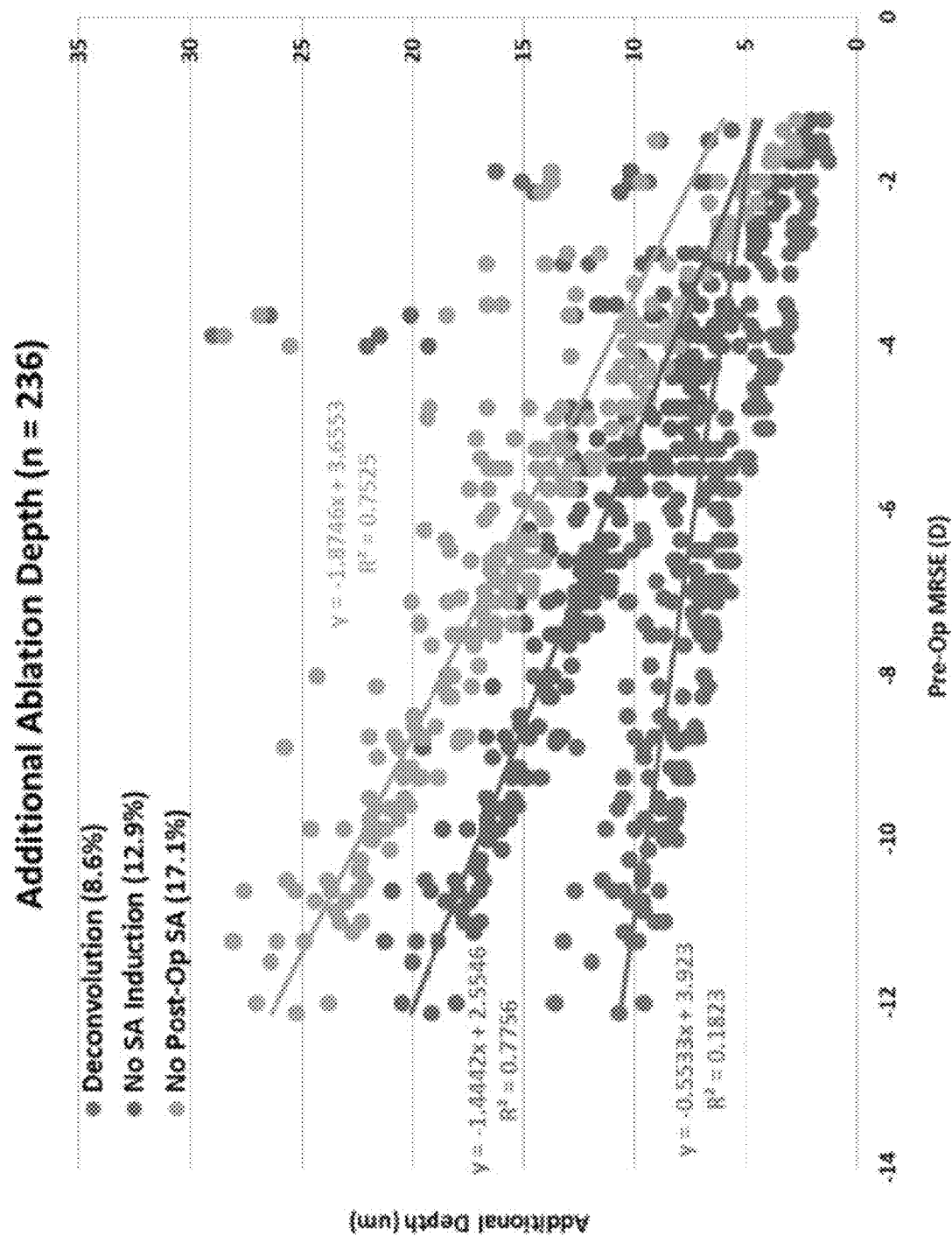
FIG. 8 is a graphical illustration of additional ablation depth resulting from deconvolution, no spherical aberration induction and no post operation spherical aberration.

A larger target slope indicates larger ablation depths and, therefore, more tissue removal. FIG. 8 is a graphical illustration of additional ablation depth (i.e., additional depth over the CV study ablation depth) resulting from deconvolution, no SA induction and no post operation SA. As shown in FIG. 8, ablation depth from deconvolution is about 8.6% deeper than the CV study ablation depth. However, as further shown in FIG. 8, an additional ablation depth 12.9% is indicated to preserve pre-op SA and an additional ablation depth of 17.1% is indicated for no post-operation SA.

Figure 9:
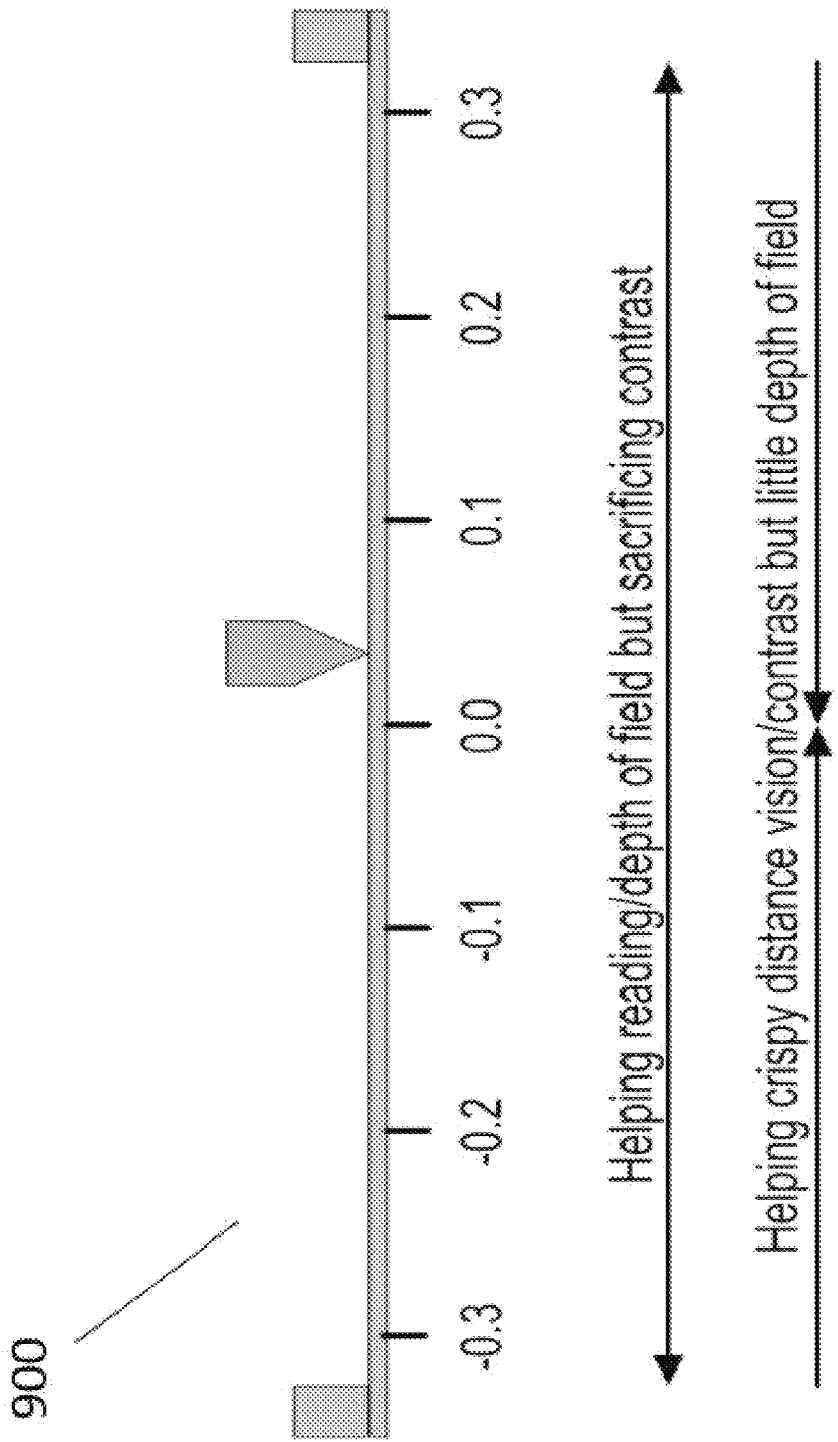
FIG. 9 is an illustration of an exemplary spherical aberration adjustment slider according to an embodiment.

The use of the PMF to reduce SA enables customized ablation designs for different eyes. For example, FIG. 9 is an illustration of an example SA adjustment slider 900 which may be used to customize an ablation designs for different patients. Because the amount of post operation SA can be controlled, the amount of post operation SA can be adjusted, for example, by displaying the SA slider 900, such that the doctor, together with the patient, can decide where to land (i.e., how much SA to remain post-operatively), using factors such as reading/depth of field vs distance vision/contrast. Customized ablation designs can help presbyopes to cope with bresnyopia.

When the target slope is determined, the PMF strength s is determined via simulation. The PMF strength s can then be used for a given refraction.

Figure 10:
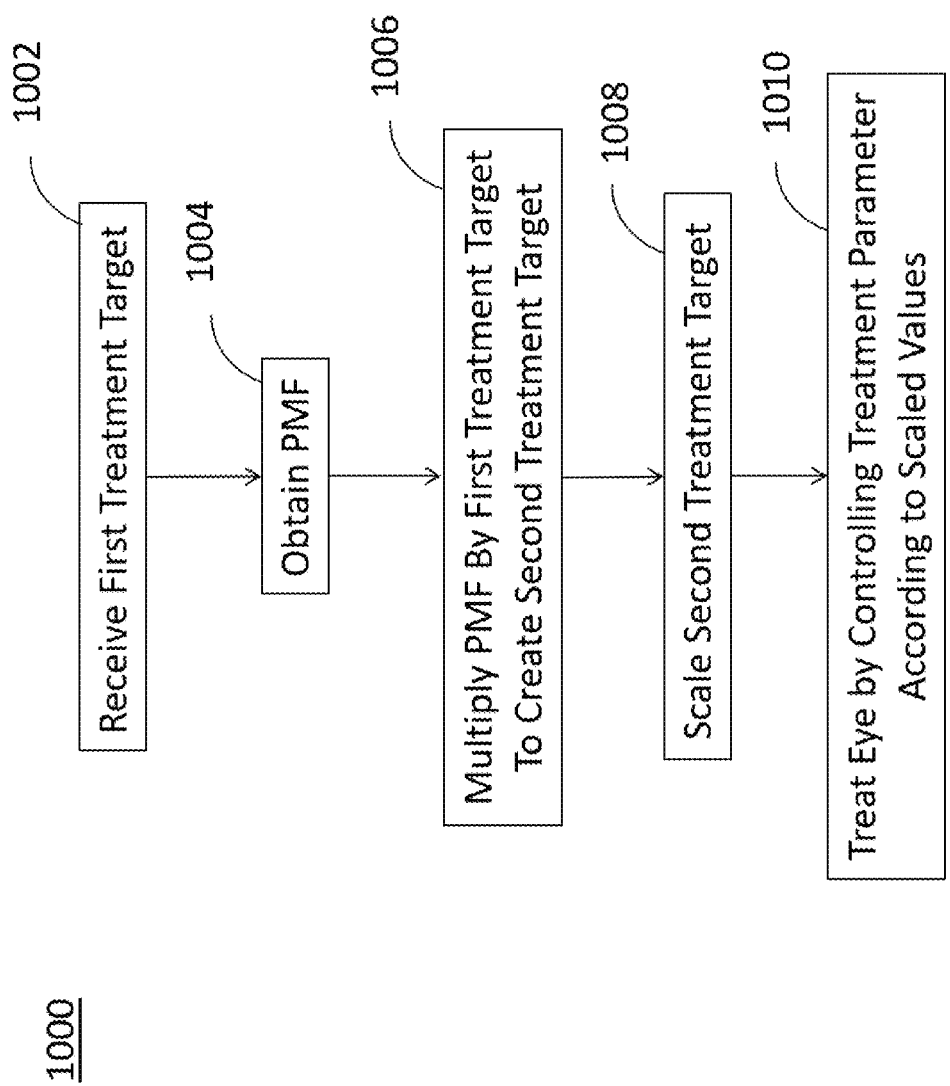
FIG. 10 is a flowchart illustrating an exemplary method of determining a vision treatment for an eye of a patient according to an embodiment.

FIG. 10 is a flowchart illustrating an example computer implemented method 1000 of determining a vision treatment for an eye of a patient. As shown at block 1002 in FIG. 10, the method includes receiving a first treatment target for the eye of the patient. For example, a treatment target, corresponding to a first shape of an optical surface of the eye, is received, by a processor. The treatment target is, for example, received from memory, a storage device or via a network.

As shown at block 1004 in FIG. 10, the method includes obtaining a PMF. For example, the PMF is estimated using the method described above including Equation 1. In Equation 1, T is the treatment target, M is the PMF, and sa is the induced SA. The modification function M is estimated as a function which increases ablation in the mid-periphery (corresponding to the regions on the graph in FIG. 4 in which the points on the PMF correspond to scaling factors above 1) and decreases ablation in the far-periphery (corresponding to regions on the graph in FIG. 4 in which the points on the PMF correspond to scaling factors below 1), in order to match the observations. The treatment target (i.e., shape of the optical surface) is increased more at the mid-periphery of the eye and decreased more at the far-periphery of the eye by adjusting a single parameter (e.g., strength s shown in FIG. 4).

As shown at block 1006 in FIG. 10, the method includes multiplying, for each of a plurality of points on a surface of the eye, the PMF by the first treatment target, to produce a second treatment target corresponding to a second shape of the optical surface of the eye. For example, for each point on the optical surface of the eye, the processor multiplies the PMF by the first treatment target to produce the second treatment target (e.g., corresponding to a modified (i.e., different) shape of the optical surface of the eye).

As shown at block 1008 in FIG. 10, the method includes scaling the modified treatment target using a scaling factor such that values of the second treatment target are scaled to be greater at a mid-periphery of the eye and less at a far-periphery of the eye. For example, referring to the PMF shown in FIG. 4, the PMF includes a bottom point 402 corresponding to scaling factor value (i.e., scaled value) of about 0.87 and a top point 404 corresponding to scaling factor value of about 1.11. As the points on the surface of the eye move further away (i.e., to the left) from the center of the eye, the PMF first includes a flat central area, followed by a mid-periphery area in which ablation is increased to point 404, followed by a decrease of ablation to point 402.

As shown at block 1010 in FIG. 10, the method includes treating the eye by controlling the treatment parameter using a scaled value. For example, the product of the PMF and the treatment target can be used to control a treatment parameter, such as an ablation depth. When any value is multiplied by 1, the product is the same as the value. Accordingly, when the PMF is multiplied by a first treatment target (e.g., an original treatment target) point-by-point, a value of 1 indicates no change to the treatment parameter. Values that are greater than 1 indicate increasing the treatment parameter and values below 1 indicate decreasing the treatment parameter. For example, if the first or previous determination is to ablate at a depth of 100 for a treatment target point on the optical surface corresponding to a scaling factor value of 1.1 on the PMF graph in FIG. 4, the resulting product of the PMF to the treatment target point indicates that the ablation depth should be changed to 110 (i.e., 100×1.1). The strength s of the PMF (i.e., difference between bottom 402 and top 404 of the PMF function) may be adjusted based on a determination of the target slope.

All patent filings, scientific journals, books, treatises, and other publications and materials discussed in this application are hereby incorporated by reference for all purposes. A variety of modifications are possible within the scope. A variety of parameters, variables, factors, and the like can be incorporated into the exemplary method steps or system modules. While the specific embodiments have been described in some detail, by way of example and for clarity of understanding, a variety of adaptations, changes, and modifications will be obvious to those of skill in the art. Although embodiments disclosed herein are described with specific reference to a wavefront system using lenslets, other suitable wavefront systems that measure angles of light passing through the eye may be employed. For example, systems using the principles of ray tracing aberrometry, tscherning aberrometry, and dynamic skiascopy may be used with embodiments disclosed herein. The above systems are available from TRACEY Technologies of Bellaire, Tex., Wavelight of Erlangen, Germany, and Nidek, Inc. of Fremont, Calif., respectively. Embodiments may also be practiced with a spatially resolved refractometer as described in U.S. Pat. Nos. 6,099,125; 6,000,800; and 5,258,791, the full disclosures of which are incorporated herein by reference. Treatments that may benefit from the embodiments include intraocular lenses, contact lenses, spectacles and other surgical methods in addition to refractive laser corneal surgery.

All features of the described systems and/or devices are applicable to the described methods mutatis mutandis, and vice versa. Each of the calculations discussed herein may be performed using a computer or other processor having hardware, software, and/or firmware. The methods or flow charts provided herein may be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

The methods and apparatuses may be provided in one or more kits for such use. The kits may comprise a system for profiling an optical surface, such as an optical surface of an eye, and instructions for use. Optionally, such kits may further include any of the other system components described in relation to the embodiments described herein and any other materials or items relevant to the embodiments. The instructions for use can set forth any of the methods as described above.

While the above provides a full and complete disclosure of exemplary embodiments, various modifications, alternate constructions and equivalents may be employed as desired. Consequently, although the embodiments have been described in some detail, by way of example and for clarity of understanding, a variety of modifications, changes, and adaptations will be obvious to those of skill in the art. Accordingly, the above description and illustrations should not be construed as limiting the embodiments, which can be defined by the claims

What is claimed is:

1. A computer implemented method of controlling ablation applied to an eye of a patient, the method comprising:

receiving a first treatment target corresponding to a first target shape of a surface of the eye;
obtaining a periphery modification function (PMF);
determining a second treatment target corresponding to a second target shape of the surface of the eye by multiplying, for each of a plurality of points on the surface of the eye, the PMF by the first treatment target;
scaling the second treatment target using a scaling factor such that values of the second treatment target are scaled to be lower at a mid-periphery of the eye and scaled to be smaller at a far-periphery of the eye; and
controlling an ablation treatment parameter of the ablation applied, by an ablation device, to the surface of the eye by the scaled second treatment target.

2. The method of claim 1, wherein the treatment parameter is an ablation depth and the method further comprises determining the ablation depth for ablating the eye at each of the plurality of points.

3. The method of claim 1, wherein the PMF is a two-dimensional function which is rotationally symmetrical with respect to a center of the eye.

4. The method of claim 1, further comprising determining, via simulation, a strength of the PMF, wherein the strength is a difference between a scaled up value of a first point on the surface and a scaled down value of a second point on the surface further from the center of the eye than the first point.

5. The method of claim 4, further comprising:
determining a target slope along points of the surface of the eye of the patient; and
adjusting the PMF based on the determined target slope.

6. The method of claim 1, further comprising:
controlling an amount of spherical aberration (SA) by the controlling of the ablation treatment parameter of the eye at each of the plurality of points.

7. The method of claim 1, wherein
the first treatment target corresponds to a first shape of an optical surface of the eye, and
the second treatment target corresponds to a second shape of the optical surface of the eye, the second shape being different from the first shape.

8. A system for controlling ablation applied to an eye of a patient, the system comprising:
a memory configured to store programmed instructions and data; and
a processor in communication with the memory and configured to:
receive a first treatment target corresponding to a first target shape of a surface of the eye;
obtain a periphery modification function (PMF);
determine a second treatment target corresponding to a second target shape of the surface of the eye by multiplying, for each of a plurality of points on the surface of the eye, the PMF by the first treatment target;
scale the second treatment target using a scaling factor such that values of the second treatment target are scaled to be greater at a mid-periphery of the eye and scaled to be lower at a far-periphery of the eye; and
control an ablation treatment parameter of the ablation applied, by an ablation device, to the surface of the eye by the scaled second treatment target.

9. The system of claim 8, wherein the treatment parameter is an ablation depth and the processor is further configured to determine the ablation depth for ablating the eye at each of the plurality of points.

10. The system of claim 8, wherein the PMF is a two-dimensional function which is rotationally symmetrical with respect to a center of the eye.

11. The system of claim 8, wherein the processor is further configured to determine, via simulation, a strength of the PMF, wherein the strength is a difference between a scaled up value of a first point on the surface and a scaled down value of a second point on the surface further from the center of the eye than the first point.

12. The system of claim 11, wherein the processor is further configured to:
determine a target slope along points of the surface of the eye of the patient; and
adjust the PMF based on the determined target slope.

13. The system of claim 8, wherein the processor is further configured to control an amount of spherical aberration (SA) by the controlling of the ablation treatment parameter of the eye at each of the plurality of points.

14. The system of claim 8, wherein
the first treatment target corresponds to a first shape of an optical surface of the eye, and
the second treatment target corresponds to a second shape of the optical surface of the eye, the second shape being different from the first shape.

15. A non-transitory computer readable medium comprising instructions for causing a computer to execute a method of controlling ablation applied to an eye of a patient, the instructions comprising:
receiving a first treatment target corresponding to a first target shape of a surface of the eye;
obtaining a periphery modification function (PMF);
determining a second treatment target corresponding to a second target shape of the surface of the eye by multiplying, for each of a plurality of points on the surface of the eye, the PMF by the first treatment target;
scale the second treatment target using a scaling factor such that values of the second treatment target are scaled to be greater at a mid-periphery of the eye and scaled to be lower at a far-periphery of the eye; and
controlling an ablation treatment parameter of the ablation applied, by an ablation device, to the surface of the eye by the scaled second treatment target.

16. The computer readable medium of claim 15, wherein the treatment parameter is an ablation depth and the instructions further comprise determining the ablation depth for ablating the eye at each of the plurality of points.

17. The computer readable medium of claim 15, wherein the PMF is a two-dimensional function which is rotationally symmetrical with respect to a center of the eye.

18. The computer readable medium of claim 15, further comprising determining, via simulation, a strength of the PMF, wherein the strength is a difference between a scaled up value of a first point on the surface and a scaled down value of a second point on the surface further from the center of the eye than the first point.

19. The computer readable medium of claim 18, wherein the instructions further comprise:
determining a target slope along points of the surface of the eye of the patient; and
adjusting the PMF based on the determined target slope.

20. The computer readable medium of claim 15, wherein the instructions further comprise:
controlling an amount of spherical aberration (SA) by the controlling of the ablation treatment parameter of the eye at each of the plurality of points.

* * * * *